United States Patent [19]

Ou

[11] Patent Number: 5,132,485

[45] Date of Patent: Jul. 21, 1992

[54] ADSORPTIVE SEPARATION OF ALPHA-OLEFINS AND INTERNAL OLEFINS

[75] Inventor: Di-Yi Ou, Houston, Tex.

[73] Assignee: Exxon Chemical Patents Inc., Linden, N.J.

[21] Appl. No.: 617,118

[22] Filed: Nov. 21, 1990

[51] Int. Cl.⁵ .............................................. C07C 7/12
[52] U.S. Cl. .................................... 585/820; 585/829
[58] Field of Search ............................... 585/820, 829

[56] References Cited

U.S. PATENT DOCUMENTS 3,150,202  9/1964  Holt et al. ............................. 585/820
3,723,561  3/1973  Priegnitz ............................... 585/820
4,119,678  10/1978  Neuzil et al. ......................... 585/829

FOREIGN PATENT DOCUMENTS 1589213  5/1981  United Kingdom .

Primary Examiner—Anthony McFarlane
Assistant Examiner—Nhat Phan
Attorney, Agent, or Firm—Linda K. Russell

[57] ABSTRACT

A process using zeolites, or molecular sieves, for separating an alpha-olefin having five or more carbons and the corresponding internal olefin or olefins. A mixture containing the alpha-olefin and one or more of the corresponding internal olefins is contacted with a zeolite which had previously undergone cation exchange. The selectivity of the zeolite, or molecular sieve, changes and eventually reverses as the carbon number increases. The selectivity is also related to the identity of the cation introduced during the cation exchange.

10 Claims, 7 Drawing Sheets

ADSORPTIVE SEPARATION OF ALPHA-OLEFINS AND INTERNAL OLEFINS

BACKGROUND OF THE INVENTION

1. Field of the Invention

The present invention is of a process for separating hydrocarbons, and, more particularly, of a process which uses zeolites, or molecular sieves, to separate alpha-olefins from internal olefins of the same carbon number.

2. Description of the Prior Art

As is well known in the art, it is often commercially desirable to separate mono alpha-olefins from internal mono olefins having the same number of carbon atoms. Mono alpha-olefins, hereinafter referred to as alpha-olefins, are olefins wherein the single double bond is located between the first and second carbon atoms. Internal mono olefins, hereinafter referred to as internal olefins, are olefins wherein the single double bond is located at a position in the molecular other than between the first and second carbon atoms.

One way to separate an alpha-olefin from the corresponding internal olefins is to take advantage of the boiling point difference of the species and use fractional distillation. However, since the boiling point difference between an alpha-olefin and a corresponding internal olefins is quite small, typically on the order of 0.6 to 10 degrees centigrade, fractional distillation requires a large number of stages and is thus often uneconomical.

It is known in the art to use zeolites, or molecular sieves, to separate 1-butene from the corresponding internal olefins, viz., isobutylene, cis-butene-2, and trans-butene-2. Such a process is taught in U.S. Pat. No. 3,723,561, wherein the separation of butene-1 from other $C_4$ mono olefins is taught. A feed stream containing the various species is contacted with a Type X or Type Y zeolite containing barium or potassium cations. The butene-1 is preferentially adsorbed onto the zeolite and is thereafter desorbed and recovered as a purified product. U.S. Pat. No. 4,119,768 teaches an improvement of the process wherein the desorption of the butene-1 is achieved using a mixture of hexene-1 and cyclohexene or cyclohexane.

It would be desirable to have a process capable of separating alpha-olefins and the corresponding internal olefins for hydrocarbons of carbon number greater than four.

SUMMARY OF THE INVENTION

The present invention successfully addresses the need for a process for separating alpha-olefins and the corresponding internal olefins for hydrocarbons of carbon number greater than four.

The present invention discloses the use of cation exchanged Type X or Type Y zeolites to separate alpha-olefins and the corresponding internal olefins. It has surprisingly been discovered that the tendency of the zeolite to preferentially adsorb the alpha-olefins generally decreases as the carbon number of the species to be separated increases. More specifically, it has been found that the selectivity of the zeolites for the alpha-olefins and the corresponding internal olefins reverses at sufficiently high carbon number, resulting in the preferential adsorption of the internal olefins. Furthermore, it has been found that the carbon number at which this selectivity reversal occurs depends on the identity of the cation with which the zeolite has been exchanged.

The process of the present invention involves the contacting of a stream containing the alpha-olefin and one or more of the corresponding internal olefins with a Type X or Type Y zeolite which has been prepared by cation exchange with a selected cation. Depending on the cation used during the exchange, and on the carbon number of the olefins to be separated, either the alpha-olefin or the internal olefins will be preferentially adsorbed onto the zeolite. The adsorbed species can then be desorbed using a desorbent or equivalent technique and the purified species recovered. The zeolite may need to be regenerated periodically to remove contaminants.

BRIEF DESCRIPTION OF THE DRAWINGS

The above and other embodiments of the present invention may be more fully understood from the following detailed description, when taken together with the accompanying drawing wherein similar reference characters refer to similar elements throughout, and in which.

DESCRIPTION OF THE PREFERRED EMBODIMENTS

The present invention is of a process for separating hydrocarbons. Specifically, the process according to the present invention uses zeolites, or molecular sieves, to separate alpha-olefins from the corresponding internal olefins of the same carbon number.

Zeolites, or molecular sieves, are well known in the art. Zeolites are crystalline aluminosilicates of Group IA and Group IIA elements such as sodium, potassium, magnesium, and calcium. They may represented by the empirical formula:

$$M_{2/n}O \cdot Al_2O_3 \cdot ySiO_2 \cdot wH_2O$$

where y is 2 or greater, n is the cation valence and represents the water contained in the voids of the zeolite. Structurally, zeolites are complex, crystalline inorganic polymers based on an infinitely extending framework of $AlO_4$ and $SiO_4$ tetrahedra linked to each other by the sharing of oxygen ions. This framework structure contains channels or interconnected voids that are occupied by the cations and water molecules. The cations are mobile and ordinarily undergo ion exchange. The water may be removed reversibly, generally by the application of heat, which leaves intact a crystalline host structure permeated by micropores which may amount to 50% of the crystals by volume.

The structural formula of a zeolite is based on the crystal cell unit cell, the smallest unit of structure, represented by the formula:

$$M_{x/n}O \cdot [(AlO_2)_x(SiO_2)_y] \cdot wH_2O$$

where n is the valence of cation M, w is the number of water molecules per unit cell, x and y are the total number of tetrahedra per unit cell, and y/x usually has values of 1 to 5.

Zeolites occur naturally but the bulk of commercially useful zeolites are synthetic. Examples of important synthetic zeolites include zeolites A, X, and Y, Zeolon H, ZSM-5 and ZSM-11. Many zeolites may be used for purposes of the present invention. In addition to those cited above, the present invention may also be practiced with zeolites such as mordenite, silicalite, beta, and others. Without in any way limiting the scope of the present invention, for purposes of the process of the present invention, attention is focused exclusively on Type X and Type Y zeolites.

Type X and Type Y zeolites are described in U.S. Pat. Nos. 2,882,244 and 3,130,007. For purposes of the present invention Type X and Type Y zeolites will be taken to include all zeolites having a general structure as represented in the two U.S. Patents above referenced.

The Type X zeolite can be represented in terms of the mole oxides as represented by the formula $$0.9 \pm 0.2 M_{2/n}O:Al_2O_3:2.5 \pm 0.5 SiO_2:wH_2O$$

where M represents at least one cation having a valence of not more than 3, n represents the valence of M and w is a value up to about 9 depending on the identity of M and the degree of hydration of the crystalline structure.

The Type Y zeolite can be represented in terms of the mole oxides for the sodium form as represented by the formula $$0.9 \pm 0.2 Na_2O:Al_2O_3:ySiO_2:wH_2O$$

where y is a value of greater than about 3 and up to about 8, and w may take on any value up to about 9.

In either Type X or Type Y zeolites it is contemplated that the zeolite will undergo partial or complete cation exchange prior to its use in the separation of alpha-olefins from the corresponding internal olefins. The cation exchanged may be any of the metals of Group IA, IIA, VIII, and IB of the Periodic Table of the Elements. Other cations not mentioned may be present in small quantities. Among the preferred cations for use according to the present invention are potassium, cesium, rubidium, strontium and barium. The preferred zeolite depends to some extent on the carbon number of the olefins to be separated. For example, K-exchanged zeolites appear to be preferred in the separation of $C_4$'s, while Ba-exchanged zeolites appear to be superior in the separation of $C_7$ to $C_{10}$ olefins.

Zeolites, also referred to as crystalline aluminosilicates, act in certain applications as molecular sieves to effect a separation of various species based on the molecular size of those species. Without in any way limiting the scope of the present invention, it is hypothesized that in the process of the present invention the functioning of the zeolites is not effected by taking advantage of the different size of the species to be separated, but is rather dependent on the different electro-chemical attraction of different isomer configurations for the zeolite surfaces, i.e. it is the selective adsorption of the isomers which is the focus of the process of the present invention.

The feed to the process of the present invention can come from any of the many refinery processes known in the art. The feed will be a mixture containing an alpha-olefin and at least one of the corresponding internal olefins, i.e. an internal olefin having the same number of carbon atoms as the alpha-olefin. The carbon number will be five or greater. Other species which may typically be present in the feed include paraffinic or naphthenic species. Also typically present will be low concentrations of aromatic hydrocarbons and other contaminant substances such as the combined sulfur nitrogen compounds. The presence of these and other contaminants will require that the zeolites be periodically regenerated so as to restore their effectiveness.

The feed will typically contain from a few percent alpha-olefin and a slightly higher fraction of total olefins to mixtures which are essentially pure olefins. The feed to the process of the present invention may be either liquid or gas. The separation operations according to the present invention can take place on either a liquid or a gaseous feed. For economic reasons, it will usually be the case that feeds which are available in the liquid phase will be separated using liquid phase separation and feeds which are available in gaseous phase will be separated using gaseous phase separation. This eliminates the need to change the phase of the feed stream and/or to operate the separation at less convenient temperatures and pressures than would otherwise be possible.

In the separation according to the present invention of light olefins such as butenes and pentenes, process temperatures could range from ambient to 60° C. For heavier olefins a processing temperature in the range of 50°-200° C. is needed to overcome diffusion limits. The processing pressure should be selected in view of the processing temperature. For liquid-phase operations the pressure should be sufficiently high so as to keep the hydrocarbons in the liquid state. For vapor-phase operations, the pressure should be higher than atmospheric and lower than the vapor pressure of the feed stream.

The zeolite used in the process of the present invention may optionally first undergo partial or complete cation exchange prior to use of the zeolite in the adsorption process.

In the process of the present invention the feed containing the species to be separated is contacted with the zeolite. Depending on the identity of the cationic species and further depending on the carbon number of the species to be separated, either the alpha-olefin or the internal olefins preferentially adsorb onto the zeolite.

Thus, the feed is separated into two components—the extract material and the raffinate, where the extract material is the component of the feed which is selectively adsorbed by the zeolite and the raffinate material includes the components of the feed which are not preferentially adsorbed by the zeolite. The raffinate may also include any extraneous species contained in the feed, such as contaminant materials.

The relative adsorption preference of the alpha-olefin and the corresponding internal olefins can be characterized through use of a selectivity parameter, which can be defined in a number of ways. For the purposes of the present invention, the selectivity of a zeolite for alpha-olefin is the dynamic selectivity defined as:

$$\text{Selectivity} = \frac{(\text{Retention volume})_p - (\text{Retention volume})_{tracer}}{(\text{Retention volume})_q - (\text{Retention volume})_{tracer}}$$

where the ratio of the two components "p" and "q", representing the alpha-olefin and the internal olefins, respectively, determine the selectivity. The "tracer" component is an inert component which is not adsorbed in the process. Thus, a selectivity greater than unity would indicate that the alpha-olefin is preferentially adsorbed. Conversely, a selectivity lower than unity would indicate that the internal olefins are preferentially adsorbed.

While it has been known in the art to use zeolite to preferentially adsorb butene-1 from a mixture also containing internal $C_4$ olefins, it has been discovered according to the present invention that it is also possible to separate alpha-olefins and the corresponding internal olefins of carbon numbers of five and higher using zeolites. Surprisingly, it has been discovered that it is not always the alpha-olefins which preferentially adsorb onto the zeolite. It has been surprisingly discovered that, as the carbon number increases, the selectivity decreases. For sufficiently high carbon number the selectivity goes below unity. In other words, whereas in the separation of isomers having four carbon atoms the alpha-olefin is preferentially adsorbed, for sufficiently high carbon numbers, it is the internal olefins which are preferentially adsorbed. Furthermore, the cation species introduced into the zeolite during cation exchange influences the selectivity of the zeolite.

Thus, for barium- or strontium-exchanged zeolites the alpha-olefin is preferentially adsorbed for a carbon number of four. The selectivity decreases with increased carbon number so that for a carbon number of seven the selectivity is reversed and it is the internal olefins which are selectively adsorbed. Similarly, for sodium- or potassium-exchanged zeolites the alpha-olefin is again preferentially adsorbed for a carbon number of four. The selectivity again decreases with increased carbon number so that for a carbon number of ten the selectivity is reversed and it is the internal olefins which are selectively adsorbed.

It is thus possible, according to the teachings of the present invention, to cause a zeolite to undergo cation exchange with a properly selected cation and thereby prepare a zeolite which will, for mono olefins of a particular carbon number, preferentially adsorb either the alpha-olefin or the internal olefins, as desired.

The separation of alpha-olefin from internal olefins may be accomplished by either adsorbing the alpha-olefin and rejecting the internal olefins, known as extractive separation, or by adsorbing the internal olefins and rejecting the alpha-olefin, which is known as rejective separation. The teachings of this invention allow, under certain circumstances, either method to be used for the purpose of producing high-purity alpha-olefin.

To complete the process, it will readily be apparent to those skilled in the art that the adsorbed species must be desorbed from the zeolite. Any number of methods for accomplishing this are known in the art. A typical desorption operation includes either the passing of a gas or a hydrocarbon material over the adsorbent in the absence of most of the raffinate. The recovery of the extract material is accomplished by the replacement of the purging of the extract material from the adsorbent.

Desorbent materials which can be included in the process of the present invention include higher molecular weight olefins, higher molecular weight olefin/paraffin mixtures, lower molecular weight olefins, or lower molecular weight olefin/paraffin mixtures, all of which are easily capable of separation from the preferentially adsorbed species.

Another commonly used desorption technique is the so-called "pressure swing" technique. According to this technique the olefins adsorbed onto the zeolite are recovered by decreasing the pressure to sub-atmospheric levels. The decrease in pressure effectuates the desorption process and is particularly useful for gas-phase processes.

As part of the process, it may also be necessary to periodically regenerate the zeolite so as to restore its effectiveness. Regeneration may be required when significant amounts of aromatics or contaminant materials such as sulfur or nitrogen compounds are present on the zeolite in a concentration large enough to reduce the selectivity and/or capacity of the zeolite below an acceptable level.

Regeneration can be carried out in a number of ways known in the art. For example, regeneration can include the removal of contaminant residues on the zeolite with steam, water or hydrocarbons at conditions to effectively flush off the contaminant materials from the zeolite. The zeolite can then be purged of the regenerant and reused in the process.

As will be readily apparent to those skilled in the art, the process according to the present invention may be implemented using a number of flow sequences. For example, the process of the present invention can be effected using a single chamber through which alternating streams of feed and desorbent are passed. Such an operation may not be appropriate for commercial scale operations.

The flow schemes which can be used to effect the process of the present invention can also include the relatively simple swing-bed operations in which one or more adsorbent beds are connected in a manner to allow adsorption and desorption operations to take place in each of the beds simultaneously with the switching of feed stock and desorbent materials between the individual adsorbent beds to effect the relatively continuous production of extract and raffinate.

Continuous production of extract and raffinate can also be made using the so-called moving bed or simulated moving bed systems. These systems generally have a higher efficiency than single-bed or simple swing-bed systems and are therefore preferred. One preferred embodiment of such systems utilizes what is known in the art as a simulated moving bed countercurrent flow system. The operating principles and sequencing of the system are described in U.S. Pat. No. 2,985,589, whose entire disclosure is incorporated by reference as if fully set forth herein. Such a system simulates the countercurrent movement of adsorbent through the progressive movement of multiple feed/- desorbent access ports along an adsorbent chamber in a direction opposite to that of the flow.

Other embodiments of a simulated moving bed flow system suitable for use in the process of the present invention may be found in U.S. Pat. Nos. 4,182,633 and 4,402,832, whose entire disclosures are incorporated by reference as if fully set forth herein.

EXAMPLES

Olefin separations were carried out using a liquid chromatograph apparatus which included an HPLC pump, a six-port feed injection valve, a ¼"×12" stainless steel adsorbent column, a pressure controller, and an automatic sampler used for periodically collecting samples of column effluent for gas chromatograph analysis.

EXAMPLE 1

Potassium-exchanged X zeolite was loaded into a 5 cc stainless steel column. The column was pre-wetted by pumping a desorbent containing 25 wt % hexene-1 and 75 wt % n-heptane at ambient temperature and at a flow rate of 2 Liquid Hourly Space Velocity (LHSV) and at 300 psi pressure until no more air bubbles were eluted. At an appropriate time, a 0.75 cc feed solution was inserted amid the desorbent flow by means of the six-port valve. Olefin adsorption and desorption took place as the section of feed solution travelled through the adsorbent column. The feed solution was composed of 3.35 wt % butene-1, 4.06 wt % trans-butene-2, 6.61 wt % cis-butene-2, 4.73 wt % 2,3-dimethyl butane and 81.25 wt % n-heptane. The 2,3-dimethyl butane served as a tracer which, in comparison with the olefins, is a relatively non-adsorbed compound. The retention volume of the tracer is related to the non-adsorbing volume in the system and is used in the calculation of the dynamic selectivity as described above.

Figure 1:
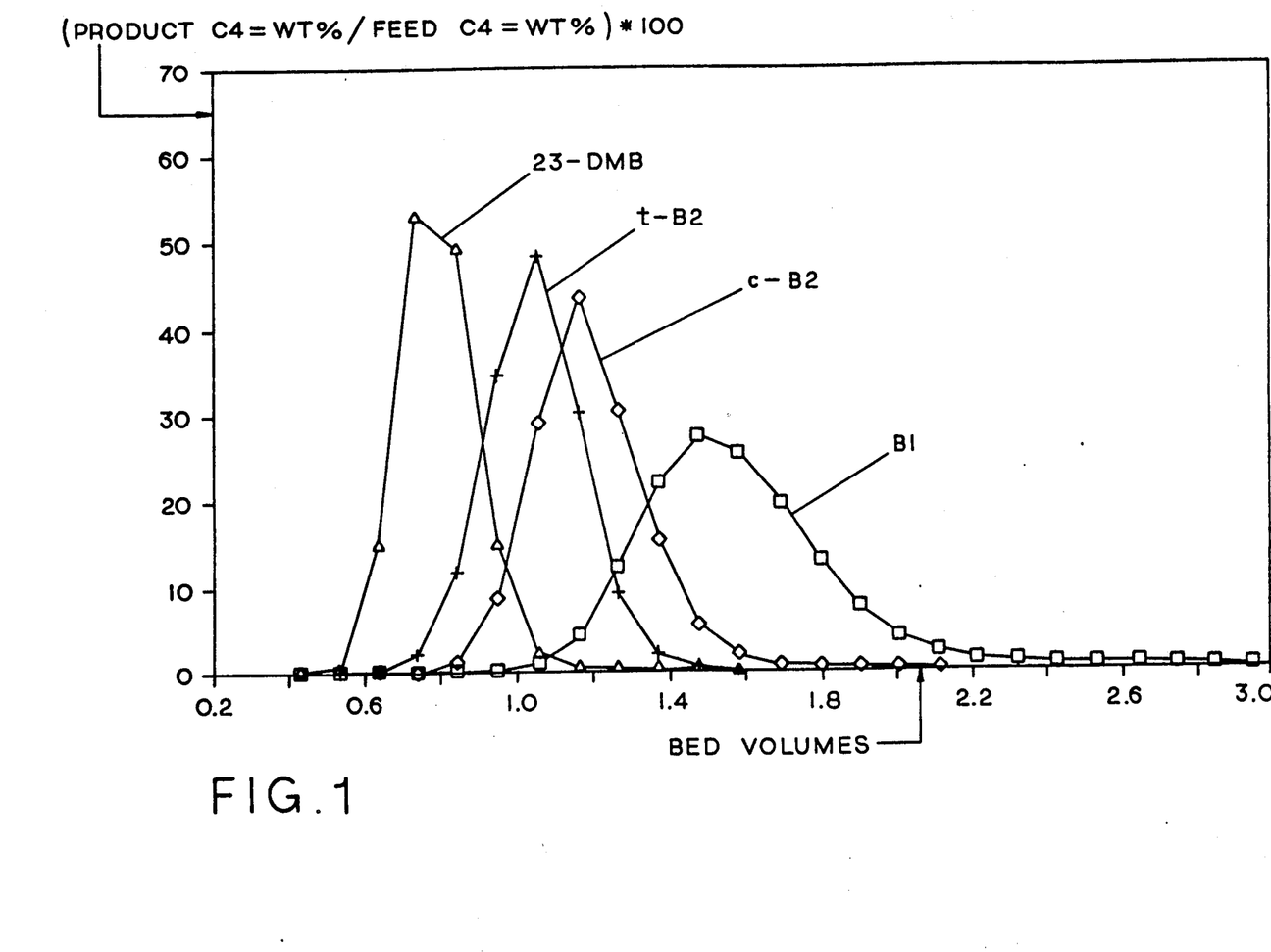
FIG. 1 is a liquid chromatograph plot depicting the separation of butene-1 from trans- and cis-butene-2 using K-exchanged X zeolite as described in Example 1.

The separation of the butenes was monitored by periodically taking effluent samples and analyzing the samples for the various butenes. The results are shown in FIG. 1. It can be seen that the potassium-exchanged Type X zeolite adsorbent caused the separation of the butene mixture by selectively adsorbing butene-1 and rejecting the cis- and trans-butene-2.

EXAMPLE 2

The procedure of Example 1 was repeated except that the feed solution used was composed of 6.32 wt % transpentene-2, 5.61 wt % pentene-1, 5.77 wt % pentane, and 82.30 wt % n-heptane. Pentane served as a tracer in this test.

Figure 2:
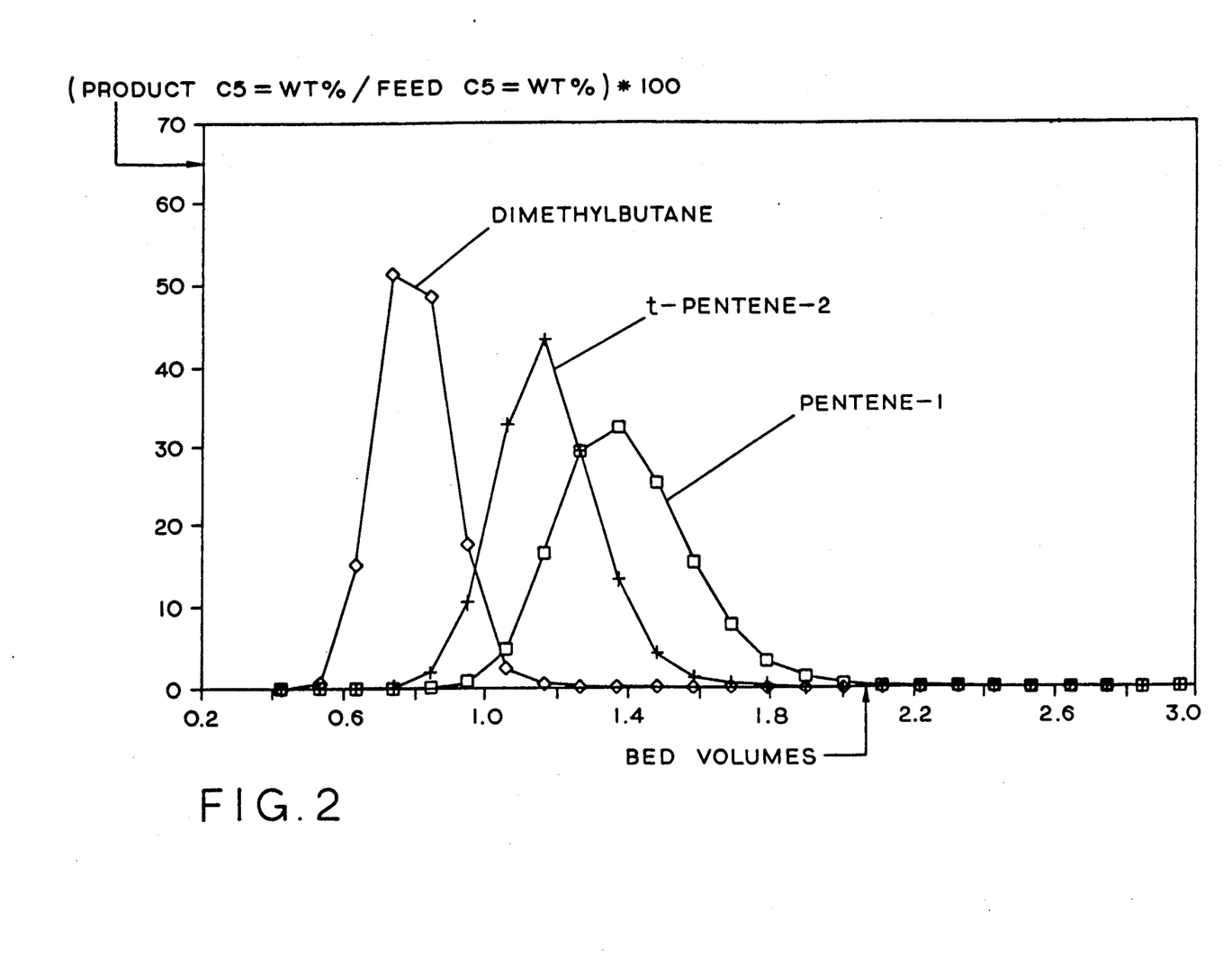
FIG. 2 is a liquid chromatograph plot depicting the separation of pentene-1 from trans-pentene-2 using K-exchanged X zeolite as described in Example 2.

The results are shown in FIG. 2. It can be seen that the potassium-exchanged Type X zeolite adsorbent separated the pentene mixture by selectively adsorbing pentene-1 and rejecting trans-pentene-2. The adsorption preference for pentene-1, however, was not as strong as for butene-1. It appeared that the zeolite gradually lost its affinity to alpha-olefins with increasing carbon number.

EXAMPLE 3

The procedure of Example 1 was repeated except that the feed solution used was composed of 5.22 wt % transheptene-2, 5.71 wt % heptene-1, 5.64 wt % 2,3-dimethyl butane, and 83.43 wt % n-heptane.

Figure 3:
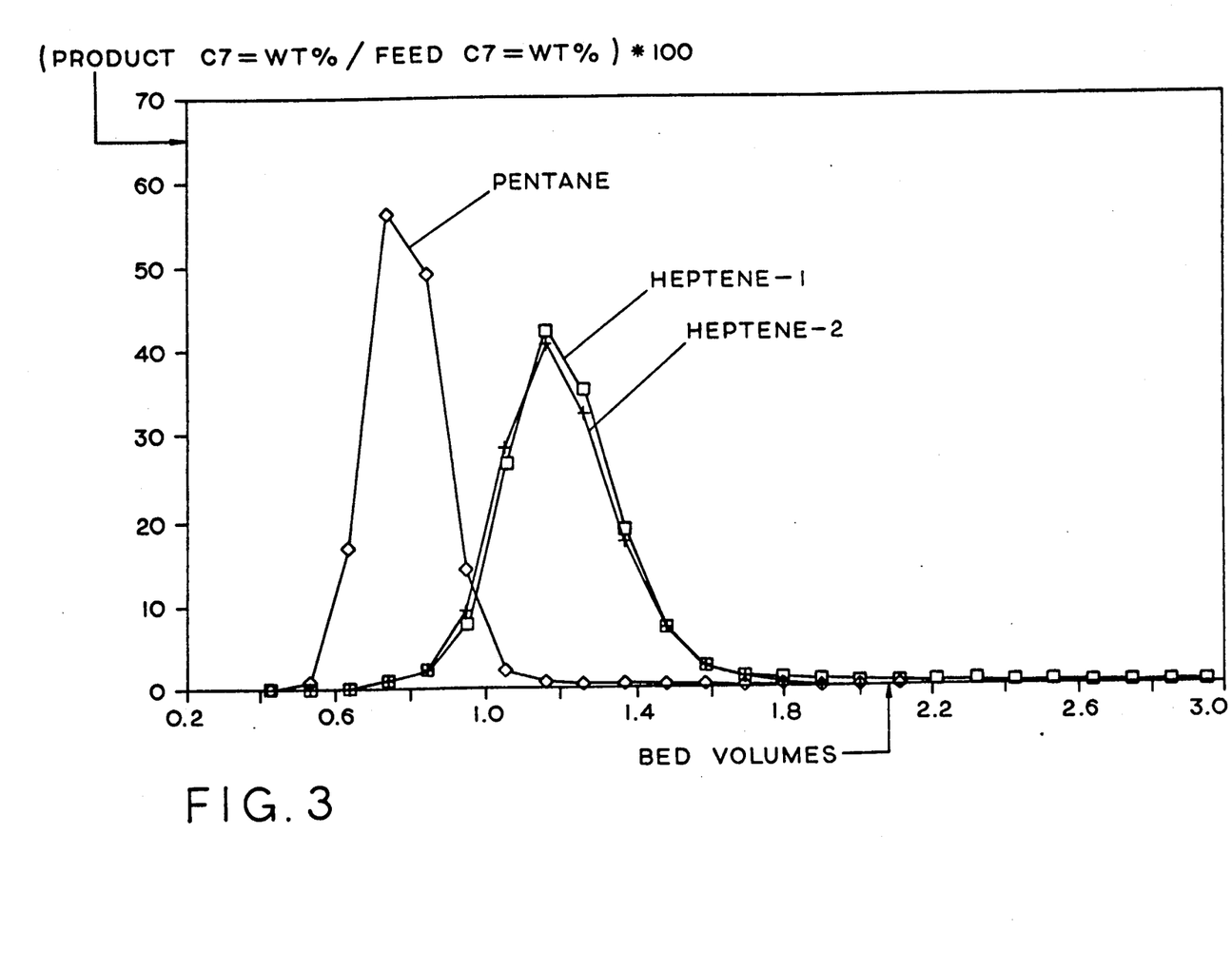
FIG. 3 is a liquid chromatograph plot depicting the separation of heptene-1 from trans-heptene-2 using K-exchanged X zeolite as described in Example 3.

The results are shown in FIG. 3. It can be seen that for molecules with a carbon number of seven, the potassium-exchanged Type X zeolite adsorbent becomes nonselective to either alpha olefin or internal olefins. Thus, the trends of decreasing affinity to alpha-olefins and increasing affinity toward internal olefins for potassium-exchanged X zeolite appears to crossover at or near the carbon number of seven. It was, therefore, anticipated that for olefins of carbon number higher than seven, the potassium-exchanged X zeolite would become more selective for internal olefins.

EXAMPLE 4

The procedure of Example 1 was repeated except that the feed solution used was composed of 5.38 wt % transdecene-5, 5.91 wt % decene-1, 5.64 wt % 2,3-dimethyl butane, and 83.07 wt % n-heptane.

Figure 4:
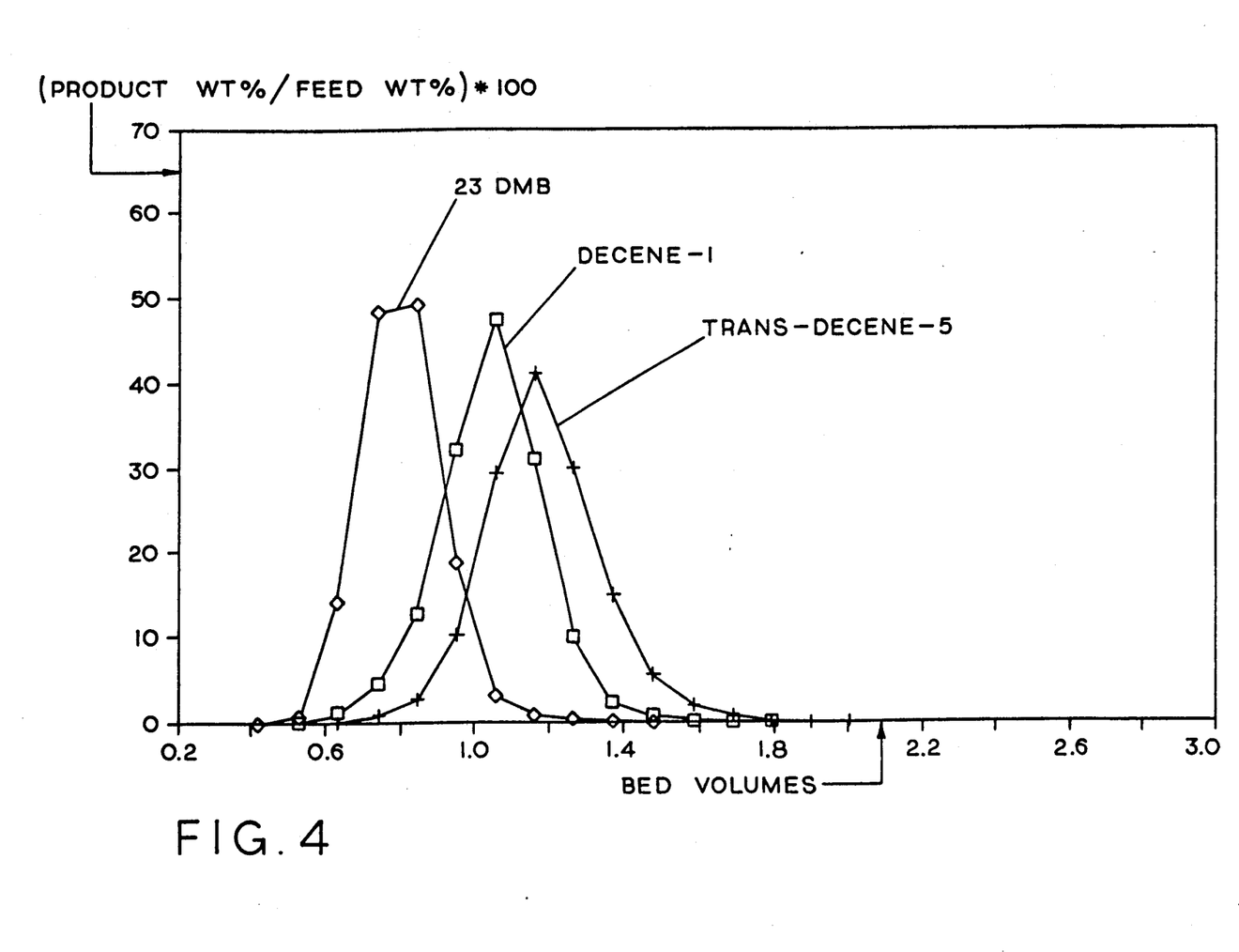
FIG. 4 is a liquid chromatograph plot depicting the separation of decene-1 from trans-decene-5 using K-exchanged X zeolite as described in Example 4.

The results are shown in FIG. 4. As expected, the potassium-exchanged X zeolite adsorbent caused the separation of the decene mixture by selectively adsorbing trans-decene-5 and rejecting decene-1.

EXAMPLE 5

Figure 5:
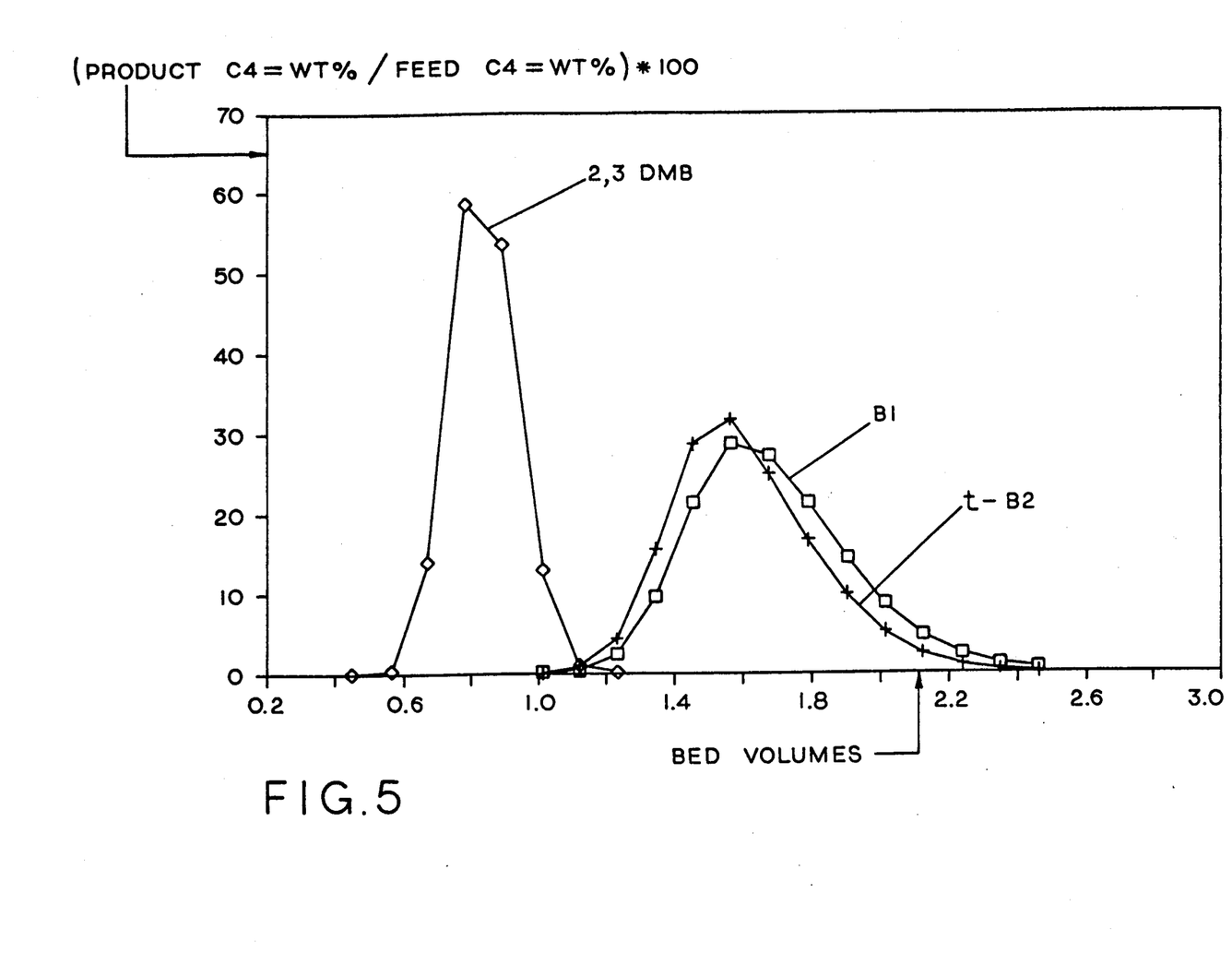
FIG. 5 is a liquid chromatograph plot depicting the separation of butene-1 from trans-butene-2 using Ba-exchanged X zeolite as described in Example 5.

The procedure of Example 1 was repeated except that the zeolite used was barium-exchanged Type X zeolite. The results are shown in FIG. 5. Although no significant olefin separation was observed, a careful inspection of the data showed that butene-1 was eluted after butene-2, indicating the alpha-olefin selectivity of barium-exchanged X zeolite for $C_4$ compounds.

EXAMPLE 6

Figure 6:
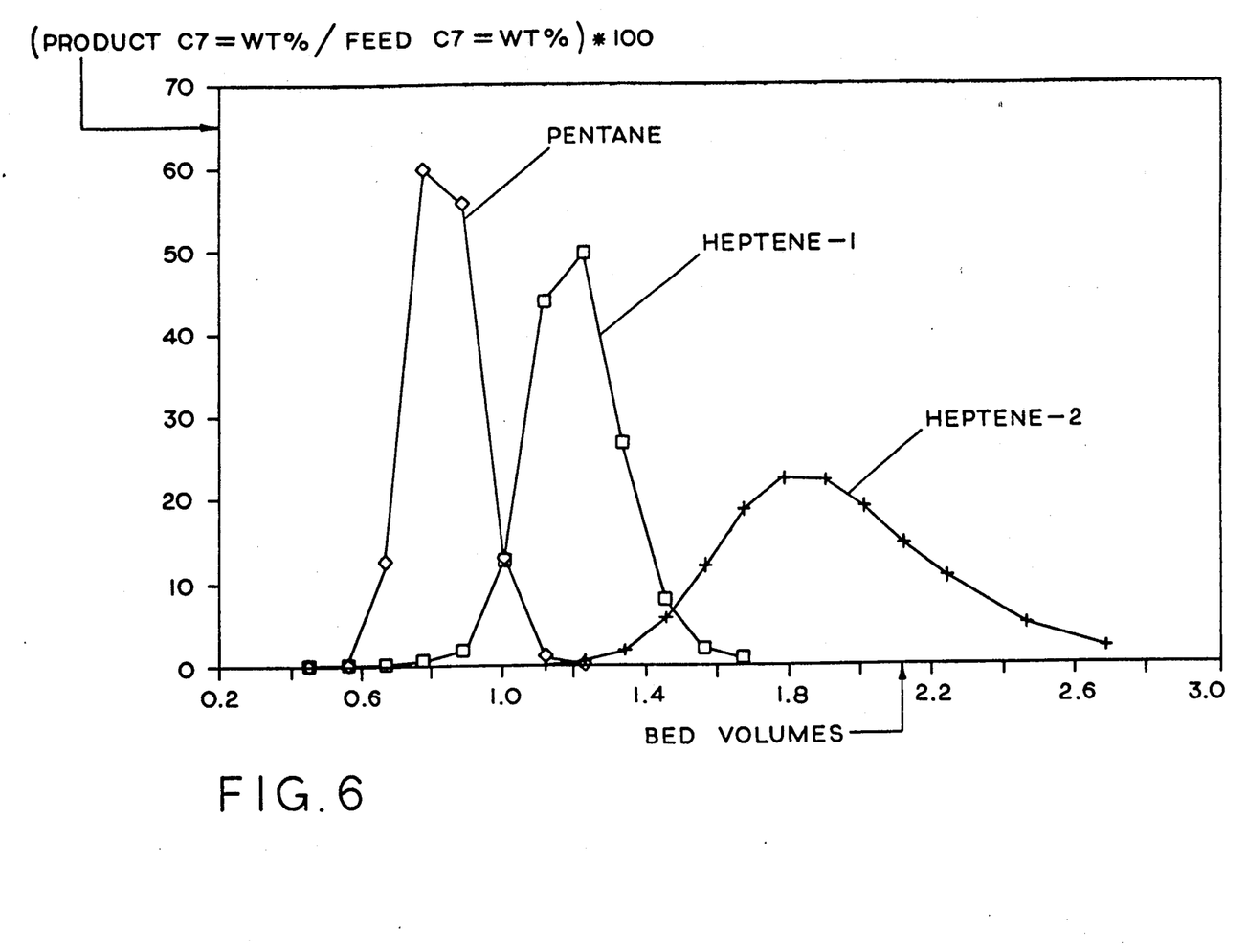
FIG. 6 is a liquid chromatograph plot depicting the separation of heptene-1 from trans-heptene-2 using Ba-exchanged X zeolite as described in Example 6.

The procedure of Example 3 was repeated except that the zeolite used was barium-exchanged Type X zeolite. The results are shown in FIG. 6. It can be seen that the heptenes were well separated and that the barium-exchanged X zeolite became selective for heptene-2.

EXAMPLE 7

Figure 7:
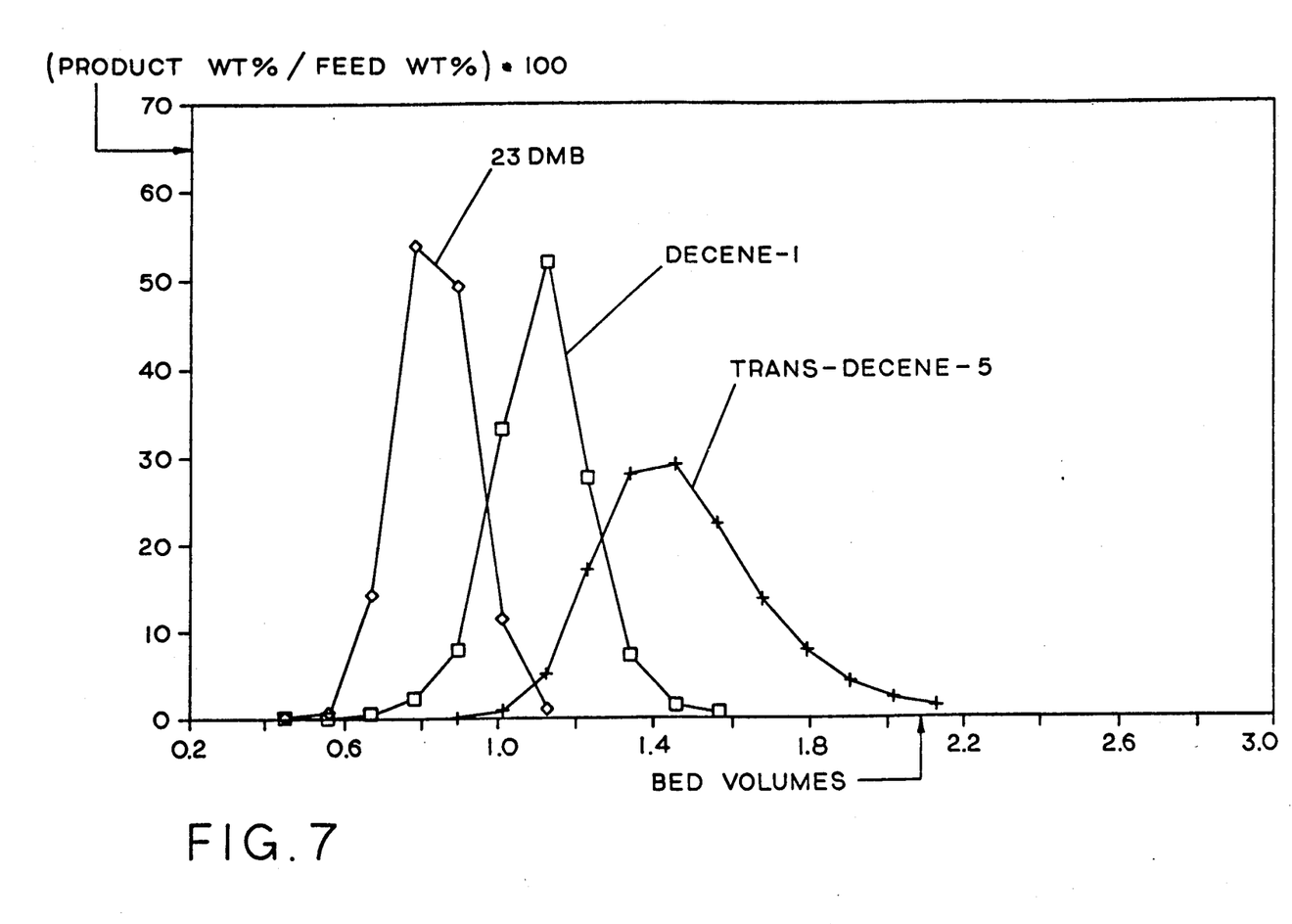
FIG. 7 is a liquid chromatograph plot depicting the separation of decene-1 from trans-decene-5 using Ba-exchanged X zeolite as described in Example 7.

The procedure of Example 4 was repeated except that the zeolite used was barium-exchanged Type X zeolite. The results are shown in FIG. 7. There was a good separation of the decenes and the barium-exchanged X zeolite remained selective toward internal olefins.

EXAMPLE 8

The procedure of Examples 5,6 and 7 were repeated except that the zeolites used were, in turn, sodium-exchanged Type X zeolite and a strontium-exchanged X zeolite. Both adsorbents separates alpha- and internal olefins and showed reversal of olefin selectivity with increasing carbon number. The dynamic selectivities for alpha-olefins in comparison to those of internal olefins determined from Examples 1-8 are summarized in the following table.

| No. of Olefin Carbons | ALPHA-OLEFIN SELECTIVITY | | | |
|---|---|---|---|---|
| | Na | K | Sr | Ba |
| 4 | 1.42 | 2.85 | 1.08 | 1.10 |
| 5 | — | 1.59 | — | — |
| 7 | 1.76 | 1.01 | 0.68 | 0.34 |
| 10 | 0.94 | 0.71 | 0.47 | 0.47 |

As can be seen the selectivity in each case decreases as the carbon number increases. As can also be seen, in each case the alpha-olefin is preferentially adsorbed (selectivity greater than unity) for lower carbon number. The selectivity reverses in each case (selectivity less than unity), indicating that for sufficiently high carbon number it is the internal olefins which are preferentially adsorbed.

This concludes the description of preferred embodiments of applicant's invention. Those skilled in the art may find many variations and adaptations thereof, and all such variations and adaptations, falling within the true scope and spirit of applicant's invention, are intended to be covered thereby.

What is claimed is:

1. A process for separating an alpha-olefin and one or more internal olefins of the same carbon number as the alpha-olefin comprising:
   (a) contacting the alpha-olefin and the one or more internal olefins with a zeolite whereby said one or more internal olefins is preferentially adsorbed by said zeolite; and
   (b) desorbing the adsorbed said one or more internal olefins from said zeolite so as to recover said adsorbed one or more internal olefins.

2. A process as in claim 1 wherein the zeolite is sodium-exchanged, potassium-exchanged, strontium-exchanged, or barium-exchanged.

3. A process as in claim 1 wherein the zeolite is zeolite X or zeolite Y.

4. A process as in claim 1 wherein the zeolite is represented by the empirical formula:

$$M_{2/n}O \cdot Al_2O_3 \cdot ySiO_2 \cdot wH_2O$$

where y is 2 or greater, n is the cation valence, and w represents the water contained in the voids of the zeolite.

5. A process as in claim 1 wherein the zeolite has a unit cell of the structural formula:

$$M_{x/n}O \cdot [(alO_2)_x(SiO_2)_y] \cdot wH_2O$$

where n is the valence of cation M, w is the number of water molecules per unit cell, x and y are the total number of tetrahedra per unit cell, and y/x has values of from 1 to about 5.

6. A process as in claim 1 wherein the zeolite is represented by the formula:

$$0.9 \pm 0.2 M_{2/n}O \colon Al_2O_3 \colon 2.5 \pm 0.5 SiO_2 \colon wH_2O$$

where M represents one or more cations having a valence of 3 or less, n is the valence of M, and w is 9 or less.

7. A process as in claim 1 wherein the zeolite is represented by the formula:

$$0.9 \pm 0.2 Na_2O \colon Al_2O_3 \colon ySiO_2 \colon wH_2O$$

where y is greater than about 3 and up to 8, and w is 9 or less.

8. A process as in claim 1 wherein the zeolite contains a metal of Group IA, IIA, VIII, and IB of the Periodic Table of Elements.

9. A process in claim 1 wherein the zeolite contains sodium, potassium, cesium, rubidium, strontium or barium.

10. A process as in claim 1 further comprising regenerating the zeolite.

* * * * *